US008524923B2

(12) United States Patent
Grushin et al.

(10) Patent No.: US 8,524,923 B2
(45) Date of Patent: Sep. 3, 2013

(54) PROCESSES FOR PREPARING DIACIDS, DIALDEHYDES AND POLYMERS

(75) Inventors: Vladimir Grushin, Tarragona (ES); Leo Ernest Manzer, Wilmington, DE (US); Walter Partenheimer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/357,985

(22) Filed: Jan. 25, 2012

(65) Prior Publication Data

US 2012/0123085 A1 May 17, 2012

Related U.S. Application Data

(62) Division of application No. 10/204,127, filed as application No. PCT/US01/09701 on Mar. 27, 2001, now Pat. No. 7,956,203.

(60) Provisional application No. 60/192,271, filed on Mar. 27, 2000.

(51) Int. Cl.
*C07D 307/24* (2006.01)
(52) U.S. Cl.
USPC .......................................................... 549/485
(58) Field of Classification Search
USPC .......................................................... 549/485
See application file for complete search history.

(56) References Cited

U.S. PATENT DOCUMENTS

| 3,007,941 A | 11/1961 | Copelin et al. |
| 4,780,552 A | 10/1988 | Wambach et al. |
| 4,977,283 A | 12/1990 | Leupold et al. |

FOREIGN PATENT DOCUMENTS

| DE | 19615878 | 10/1997 |
| JP | 54009260 | 1/1974 |
| JP | 55049368 | 3/1980 |

OTHER PUBLICATIONS

R. A. Sheldon et al., Metal Catalyzed Oxidations of Organic Compounds, Academic Press (1981), p. 107-32.
L. Cottier et al., Org. Prep. Proced. Int., vol. 27, Issue 5 (1995), p. 564-566.
C. Moreau et al., Stud. Surf. Sci. Catal., vol. 108 (1997), pp. 399-406.
M.P.J. Van Deurzen, Carbohydrate Chem., vol. 16, Issue 3 (1997), p. 299-309.
V.A. Slavinskaya et al., React. Kinet. Catal. Lett., vol. 11, Issue 3 (1979), pp. 215-220.
Cooke et al., Macromolecules, vol. 24, (1991), p. 1404-1407.
Sheldon, R.A., et al. "Metal Catalyzed Oxidations of Organic Compounds", Academic Press, (1981), p. 19, New York, New York.
L. Cottier, et al. Org. Prep. Proced. Int. (1995), p. 27, vol. 5, Issue 564.
C. Moreau, et al., "Stud. Surf. Sci. Catal." (1997), pp. 399-406, vol. 108.
M.P.J. Van Deurzen, "Carbohydrate Chem", (1997), pp. 299, vol. 16, Issue 3.
W. Partenheimer, "Catalysis Today", (1995) pp. 69-158, vol. 23, Issue 2.
V.A. Slavinskaya, et al., "React. Kinet. Catal. Lett." (1979), pp. 215-220, vol. 11, Issue 3.
Cooke, et al. Macromolecules (1991), p. 24. vol. 1404.
R. A. Sheldon et al., Metal Catalyzed Oxidations of Organic Compounds, Academic Press (1981), p. 19.
L. Cottier et al., Org. Prep. Proced. Int., vol. 5. Issue 564 (1995), p. 27.
C. Moreau et al, Stud. Surf. Sci. Catal., vol. 108 (1997), pp. 399-406.
M.P.J. Van Deurzen, Carbohydrate Chem., vol. 16, Issue 3 (1997), p. 299.
W. Partenheimer, Catalysis Today, vol. 23. Issue 2 (1995), pp. 69-158.
V.A. Slavinskaya et al., React. Kinet. Catal. Lett., vol. 11. Issue 3 (1979), pp. 215-220.
Cooke et al., Macromolecules, vol. 1404 (1991), p. 24.

*Primary Examiner* — Bernard Dentz

(57) ABSTRACT

Alcohols are catalytically oxidized to aldehydes, in particular to benzaldehyde and diformylfuran, which are useful as intermediates for a multiplicity of purposes. The invention also relates to the polymerization of the dialdehyde and to the decarbonylation of the dialdehyde to furan.

9 Claims, No Drawings

PROCESSES FOR PREPARING DIACIDS, DIALDEHYDES AND POLYMERS

FIELD OF INVENTION

The invention relates to the catalytic oxidation of alcohols to aldehydes, in particular the formation of benzaldehyde and diformylfuran, which are useful as intermediates for a multiplicity of purposes. The invention also relates to the polymerization and the decarbonylation of a dialdehyde.

BACKGROUND 5-(Hydroxymethyl)furfural (HMF) is a versatile intermediate that can be obtained in high yield from biomass sources such as naturally occurring carbohydrates, including fructose, glucose, sucrose, and starch. Specifically, HMF is a conversion product of hexoses with 6 carbon atoms. It is known that HMF can be oxidized using a variety of reagents to form any of four different products, which can themselves be converted to one or more of the others:

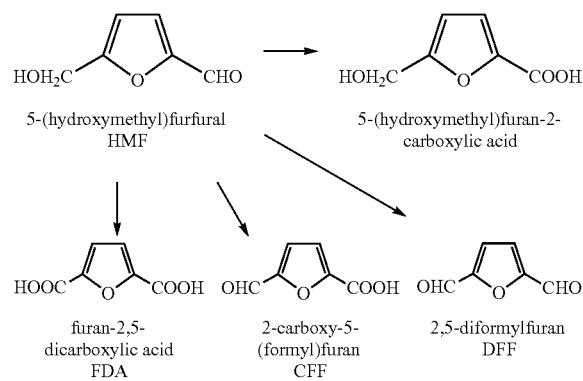

The selective oxidation of an alcohol functionality in the presence of an aldehyde functionality on the same compound is difficult because of the high reactivity of the aldehyde group. Furthermore, if HMF is reacted with molecular oxygen ($O_2$), the aldehyde functionality would be expected to oxidize more rapidly than the alcohol and the expected product would be predominantly 5-(hydroxymethyl)furan-2-carboxylic acid (Sheldon, R. A. and Kochi, J. K. "Metal Catalyzed Oxidations of Organic Compounds", Academic Press, New York, N.Y. 1981, p 19).

Diformylfuran (DFF) has been prepared from HMF using $CrO_3$ and $K_2Cr_2O_7$ (L. Cottier et al., *Org. Prep. Proced. Int.* (1995), 27(5), 564; JP 54009260) but these methods are expensive and results in large amounts of inorganic salts as waste. Heterogeneous catalysis using vanadium compounds has also been used, but the catalysts have shown low turnover numbers (DE 19615878, Moreau, C. et al., *Stud. Surf. Sci. Catal.* (1997), 108, 399-406). Catalytic oxidation has been demonstrated using hydrogen peroxide (M. P. J. Van Deurzen, *Carbohydrate Chem.* (1997), 16(3), 299) and dinitrogen tetraoxide (JP 55049368) which are expensive. The relatively inexpensive molecular oxygen ($O_2$) has been used with a Pt/C catalyst (U.S. Pat. No. 4,977,283) to form both DFF and furan-2,5dicarboxylic acid (FDA), but yielded low amounts of DFF. Good yields were found for FDA, but only as the disodium salt which resulted in wasteful salt formation during conversion to the acid form.

Metal bromide catalysts have been used to oxidize substituted alkylbenzenes to various products including the oxidation of alkyl to aldehydes, alkyl to alcohols, alkyl to acids, alcohol to acid, and aldehydes to acids (W. Partenheimer, *Catalysis Today*, 23(2), 69-158, (1995)). However, in such cases, the aldehyde product is either a minor component or is quickly oxidized further. FDA has also been prepared using a Co/Mn/Br catalyst from 5-methylfurfural with DFF seen as a minor byproduct (V. A. Slavinskaya, et al., *React. Kinet. Catal. Lett.* (1979), 11(3), 215-20).

DFF has been polymerized to form polypinacols and polyvinyls (Cooke, et al., *Macromolecules* 1991, 24, 1404). However, preparation of polyesters prepared from diformylfuran is not known in the literature.

DFF can also be used to produce unsubstituted furan. Unsubstituted furan is an important commodity in the chemical industry used in the production of tetrahydrofuran. Supported metal catalysts have been used in the decarbonylation of the monoaldehyde furfural to furan, but a basic promoter is required, adding expense and complexity to the process (U.S. Pat. No. 3,007,941, U.S. Pat. No. 4,780,552).

Considering the aforementioned discussion, there is a need for an inexpensive, high yield process for the preparation of both DFF and FDA that does not produce large amounts of waste products and which lends itself to easy separation and purification. Additionally, there is a need for a high yielding process to prepare unsubstituted furan from relatively inexpensive, renewable sources.

SUMMARY OF THE INVENTION

The invention is directed to a first process for the preparation of a dialdehyde comprising a) contacting a compound containing an alcohol functionality and an aldehyde functionality with an oxidant in the presence of a metal bromide catalyst; and b) optionally isolating the dialdehyde product. A preferred metal bromide catalyst comprises a source of bromine and at least one metal selected from the group consisting of Co and Mn, and optionally containing Zr. More preferably the metal bromide catalyst contains Co.

Preferably the dialdehyde is of the formula H(C=O)—R—(C=O)H and the compound is of the formula $HOH_2C$—R—(C=O)H, wherein R is selected from the group consisting of an optionally substituted $C_1$-$C_{20}$ alkyl or aryl group. The R groups can be linear or cyclic, or a heterocyclic group. More preferably, R is furan, and most preferably the dialdehyde is 2,5-di(formyl)furan. The process of the present invention can be run in a solvent mixture comprising at least one aliphatic $C_2$-$C_6$ monocarboxylic acid compound, preferably acetic acid.

The invention is further directed to a second process for the preparation of a diacid of the formula HOOC—R'—COOH from an alcohol/aldehyde of the formula $HOH_2C$—R'—(C=O)H, wherein R' is an optionally substituted furan ring, comprising the steps:

(a) contacting the alcohol/aldehyde with an oxidant in the presence of a metal bromide catalyst forming an alcohol/acid having the formula $HOH_2C$—R'—COOH, and optionally isolating the alcohol/acid;

(b) contacting the alcohol/acid with an oxidant in the presence of a metal bromide catalyst forming an acid/aldehyde having the formula HOOC—R'—(C=O)H, and optionally isolating the acid/aldehyde;

(c) contacting the acid/dialdehyde with an oxidant in the presence of a metal bromide catalyst forming the diacid, optionally isolating the diacid.

The invention is further directed to a third process for the preparation of a diacid of the formula HOOC—R'—COON from an alcohol/aldehyde of the formula HOH₂C—R'—(C=O)H, wherein R' is an optionally substituted furan ring, comprising the steps:
- (a') contacting the alcohol/aldehyde with an oxidant in the presence of a metal bromide catalyst forming a dialdehyde having the formula H(C=O)—R'—(C=O)H, and optionally isolating the dialdehyde;
- (b') contacting the dialdehyde with an oxidant in the presence of a metal bromide catalyst forming an acid/aldehyde having the formula HOOC—R'—(C=O)H, and optionally isolating the acid/aldehyde; and
- (c') contacting the acid/dialdehyde with an oxidant in the presence of a metal bromide catalyst forming the diacid, and optionally isolating the diacid.

The process further comprises the steps of a', b', and c' and wherein the alcohol/aldehyde of the formula HOH₂C—R'—(C=O)H is converted to an acetate ester of the formula CH₃(C=O)OCH₂—R'—(C=O)H.

Preferably, in the above process the diacid is furan-2,5dicarboxylic acid and the alcohol/aldehyde is 5-(hydroxymethyl)furfural.

The process can optionally be run in a solvent or solvent mixture comprising at least one aliphatic C₂-C₆ monocarboxylic acid compound, preferably acetic acid.

The invention is also directed to a fourth process for the preparation of an aldehyde comprising a) contacting a compound of the formula AR—CH₂—OH wherein AR is an optionally substituted aryl with an oxidant in the presence of a metal bromide catalyst; and b) optionally isolating the aldehyde product. Preferably, AR an optionally substituted phenyl group. Most preferably, AR is an unsubstituted phenyl group. A preferred metal bromide catalyst is comprised of a source of bromine and at least one metal selected from the group consisting of Co and Mn. More preferably the metal bromide catalyst contains Co.

The process can be run in a solvent or solvent mixture comprising at least one aliphatic C₂-C₆ monocarboxylic acid compound, preferably acetic acid.

The invention is also directed to a fifth process to form a polyester polymer and the polyester polymer so produced from 2,5-diformylfuran comprising the repeat units A and B and C.

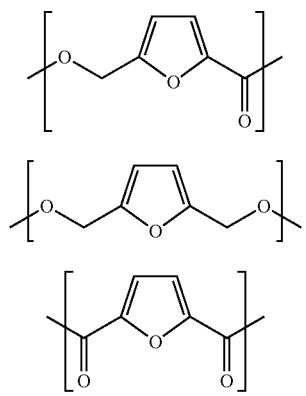

wherein said process comprises polymerization of di(formyl)furan. The process can be performed in the presence of a catalyst of the formula M⁺ⁿ(O-Q)ₙ wherein M is a metal, n is the positive charge on the metal, and Q is an alkyl group of 1-4 carbons. Preferably, M is aluminum and n is three. Preferably the polyester polymer formed from the process is a homopolymer.

An embodiment of the invention is a polyester polymer comprising repeating units A, B and C. Preferably, the polyester polymer is a homopolymer.

Another aspect of the invention is a sixth process for the preparation of furan comprising converting 2,5-diformylfuran into furan and furfural via decarbonylation in the presence of a catalytic amount of a compound consisting essentially of a optionally supported metal selected from Periodic Group VIII. The furan and furfural product may further be converted via decarbonylation into unsubstituted furan in the presence of a catalytic amount of a compound consisting of an optionally supported metal selected from Periodic Group VIII.

Preferably the catalyst is supported on a catalyst support member, more preferably the metal is palladium and the catalyst support member is carbon.

Another aspect of the invention is to convert the dialdehyde prepared using the above processes, wherein the dialdehyde is 2,5-di(formyl)furan, into furan via decarbonylation in the presence of a catalytic amount of a compound consisting of a optionally supported metal selected from Periodic Group VIII.

DETAILED DESCRIPTION

The present invention concerns a first process for the preparation of a dialdehyde comprising contacting a first compound containing an alcohol functionality and an aldehyde functionality with an oxidant in the presence of a metal bromide catalyst. More specifically, the alcohol can be HMF, the dialdehyde can be DFF, and the catalyst can be comprised of Co and/or Mn, and Br, and optionally Zr.

In addition to the alcohol and the aldehyde, other functional groups may be attached to the first compound as long as the other functional groups are substantially inert under reaction conditions. In a preferred process the first compound is of the formula HOH₂C—R—(C=O)H, and the resulting dialdehyde product that is prepared is of the formula H(C=O)—R—(C=O)H. In the above formula for the first compound and the dialdehyde product of this invention, R is selected from the group consisting of an optionally substituted C₁-C₂₀ alkyl and optionally substituted C₁-C₂₀ aryl group. The R groups are either linear, cyclic, or heterocyclic. More preferred is where R is selected from the group consisting of an optionally substituted C₁-C₂₀ alkyl group, linear or cyclic, and a heterocyclic group. Most preferred is where R is a furan. By optionally substituted herein is meant a group that may be substituted and may contain one or more substituent groups that do not cause the compound to be unstable or unsuitable for the use or reaction intended. Substituent groups which are generally useful include nitrile, ether, alkyl, ester, halo, amino (including primary, secondary and tertiary amino), hydroxy, silyl or substituted silyl, nitro, and thioether.

The term "aryl" refers to an aromatic carbo-cyclic group having a single ring (e.g., phenyl), multiple rings (e.g., biphenyl), or multiple condensed rings of which at least one is aromatic (e.g., 1,2,3,4-tetrahydronaphthyl, naphthyl, anthryl, or phenanthryl), and which is optionally mono-, di-, or tri-substituted with a functional group such as halogen, lower alkyl, lower alkoxy, lower alkylthio, trifluoromethyl, lower acyloxy, aryl, heteroaryl, and hydroxy. The term "aryl" also refers to heteroaryl groups where heteroaryl is defined as 5-, 6-, or 7-membered aromatic ring systems having at least one hetero-atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

A particularly preferred process is where R is 2,5-disubstituted furan, i.e., where the first compound is HMF and the dialdehyde is DFF.

DFF may be further converted via loss of CO to furan, which can be hydrogenated to tetrahydrofuran using standard techniques familiar to those skilled in the art.

The second process concerns preparation of a diacid of the formula HOOC—R'—COON from an alcohol/aldehyde of the formula $HOH_2C$—R'—(C=O)H.

The third process concerns preparation of a diacid of the formula HOOC—R'—COON from an alcohol/aldehyde of the formula $HOH_2C$—R'—(C=O)H.

In the second and third processes, R' is preferably an optionally substituted furan ring. More preferably, R' is a 2,5-disubstituted furan ring. A preferred metal bromide catalyst is comprised of a source of bromine and at least one metal selected from the group consisting of Co and Mn, and optionally containing Zr. More preferably the metal bromide catalyst contains Co.

Any of the intermediates, the alcohol/acid, acid/aldehyde, or the dialdehyde, may be isolated at any step, or the reaction may proceed without any purification. It is contemplated that the processes of the invention in which DFF and/or FDA is prepared can be run using a biomass feedstock containing HMF, such that only the final product need be isolated and purified.

For the preparation of the dialdehyde, the preferred temperatures are about 20° to 200° C., most preferably about 40° to 130° C. The corresponding pressure is such to keep the solvent mostly in the liquid phase. The preferred time of the reaction is determined by the temperature, pressure, and catalyst concentration such that maximum yield of dialdehyde is obtained. For preparation of diacid, the preferred temperatures are about 50° to 250° C., most preferentially about 50° to 160° C. The corresponding pressure is such to keep the solvent mostly in the liquid phase. The preferred time of the reaction is determined by the temperature, pressure and catalyst concentration such that a maximum yield of diacid is obtained.

The fourth process concerns preparation of an aldehyde comprising contacting a compound of the formula AR—$CH_2$—OH, wherein AR is an optionally substituted aryl group, with an oxidant in the presence of a metal bromide catalyst. Preferably, AR an optionally substituted phenyl group. Most preferably, AR is an unsubstituted phenyl group. In addition to the alcohol, other functional groups may be attached to the compound as long as the other functional groups are substantially inert under reaction conditions.

A preferred metal bromide catalyst is comprised of a source of bromine and at least one metal selected from the group consisting of Co and Mn, and optionally containing Zr. More preferably the metal bromide catalyst contains Co.

The process can be run in a solvent or solvent mixture comprising at least one aliphatic $C_2$-$C_6$ monocarboxylic acid compound, preferably acetic acid.

Metal bromide catalysts employed in all of the processes of this invention comprise a soluble transition metal compound and soluble bromine-containing compound. One metal or a combination of two or more metals may be present. Many such combinations are known and may be used in the processes of the instant invention. These metal bromide catalysts are described further in W. Partenheimer, *Catalysis Today*, 23(2), 69-158, (1995), in particular pages 89-99, herein incorporated by reference. Preferably the metal is cobalt and/or manganese, optionally containing zirconium. More preferably, the catalyst is comprised of Co/Mn/Zr/Br in the molar ratios of 1.0/1.0/0.1/2.0. The amount of catalyst in the reaction mixture can be 59/55/203/4 ppm to 5900/5500/20000/390 ppm Co/Mn/Br/Zr, preferably 150/140/510/10 ppm to 2400/2200/8100/160 ppm (g of metal/g of solvent). As used herein, the molar ratio is the ratio of moles of the metals alone, not the metals as in their compound forms.

Each of the metal components can be provided in any of their known ionic or combined forms. Preferably the metal or metals are in a form that is soluble in the reaction solvent. Examples of suitable forms include, but are not limited to, metal carbonate, metal acetate, metal acetate tetrahydrate, and metal bromide. Preferably metal acetate tetrahydrates are used.

The source of bromide can be any compound that produces bromide ions in the reaction mixture. These compounds include, but are not limited to, hydrogen bromide, hydrobromic acid, sodium bromide, elemental bromine, benzyl bromide, and tetrabromoethane. Preferred is sodium bromide or hydrobromic acid. As used herein, the amount of bromine means the amount measured as Br. Thus, the molar ratio of bromine to total of the metals used in the catalyst is the moles of Br divided by the sum of the moles of the metal.

As described in Partenheimer, ibid, pages 86-88, suitable solvents for use in the processes of the present invention, described above, must have at least one component that contains a monocarboxylic acid functional group. The solvent may also function as one of the reagents. The processes may be run in a solvent or solvent mixture that does not contain an acid group, provided that one of the reagents does contain such a group. Suitable solvents can also be aromatic acids such as benzoic acid and derivatives thereof. A preferred solvent is an aliphatic $C_2$-$C_6$ monocarboxylic acid, such as but not limited to acetic acid, propionic acid, n-butyric acid, isobutyric acid, n-valeric acid, trimethylacetic acid, and caproic acid and mixtures thereof. Components of said mixtures can include benzene, acetonitrile, heptane, acetic anhydride, chlorobenzene, o-dichlorobenzene, and water. Most preferred as solvent is acetic acid. One advantage of using a solvent such as acetic acid is that furan-2,5-dicarboxylic acid is insoluble, facilitating purification of the insoluble product.

The oxidant in the processes of the present invention is preferably an oxygen-containing gas or gas mixture, such as, but not limited to air. Oxygen by itself is also a preferred oxidant.

The processes of the instant invention described above can be conducted in the batch, semi-continuous or continuous mode. Especially for the manufacture of FDA, operation in the batch mode with increasing temperature at specific times, increasing pressure at specific times, variation of the catalyst concentration at the beginning of the reaction, and variation of the catalyst composition during the reaction is desirable. For example, variation of the catalyst composition during reaction can be accomplished by addition of cobalt and/or manganese and/or zirconium, and/or bromide at specified times.

The fifth process concerns the polymerization of di(formyl)furan to form a novel polyester polymer comprising the repeat units A, B and C, as shown in the summary above. The catalysts employed in the polymerization of di(formyl)furan can be selected from any catalyst used for the esterification of a dialdehyde or two separate aldehydes. This esterification is commonly known as the "Tishchenko reaction". A partial list of catalysts used for this reaction are those listed in Mascarenhas, et al., *Org. Letters,* 1999, Vol. 1, 9, pg. 1427; U.S. Pat. No. 3,852,335; and *Reagents for Organic Synthesis,* Fieser (ed.), 1969, Vol. 5, pg. 48, and are herein incorporated by reference. An alternate catalyst is the Shvo catalyst, [(Ph$_4$C$_5$OHOC$_5$Ph$_4$)Ru$_2$(CO)$_4$(—H)], as described in Menashe, et al., *Organometallics* 1991, 10, 3885. This discussion concerning the Shvo catalyst is also incorporated herein by reference. Preferred catalysts are metal alkoxides of the formula M+$n$(O-Q)$_n$ where M is a metal, n is the positive charge on the metal, and Q is an alkyl group of 1-4 carbons. Most preferred is where M is aluminum and n is three. The catalysts of the invention can be obtained already prepared from manufacturers, or they can be prepared from suitable starting materials using methods known in the art.

The repeat units A, B, and C can all be present in the polyester polymer product but are present in varying ratios, in any order in which an ester linkage is present and a polyester is formed. The term polymer is herein defined to include oligomers of 3 or more repeating units as well as higher polymers. This polymer would be useful as a molding resin or may be spun into a fiber.

The polyester polymer produced by the present process may include other repeat units in addition to those shown above. Other polyesters having the above repeat units include, but are not limited to, polyesteramides, polyesterimides, and polyesterethers. A preferred version of the polymer is a homopolymer.

A preferred embodiment of the present invention is the catalytic decarbonylation of DFF to form a mixture of unsubstituted furan and furfural.

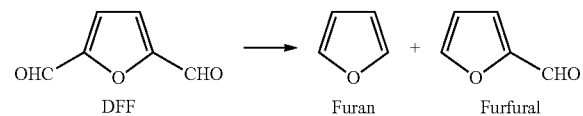

in the presence of a catalytic amount of a metal selected from Periodic Group VIII, herein defined as Fe, Ru, Os, Co, Rh, Ir, Ni, Pd, and Pt. Preferably, the catalyst consists essentially of one or more of the Periodic Group VIII metals. A particularly preferred catalyst consists essentially of Pd.

The metals may be in any form including Raney catalysts as known to those skilled in the art. The catalysts are preferably supported on a catalyst solid support. The catalyst solid support, which includes but not limited to, SiO$_2$, Al$_2$O$_3$, carbon, MgO, zirconia, or TiO$_2$, can be amorphous or crystalline, or a mixture of amorphous and crystalline forms. Selection of an optimal average particle size for the catalyst supports will depend upon such process parameters as reactor residence time and desired reactor flow rates. The amount of metal on the support is preferably about 0.5-10% and most preferably 1-5%. The catalysts of the invention can be obtained already prepared from manufacturers, or they can be prepared from suitable starting materials using methods known in the art. One typical procedure is by impregnation of the support by incipient wetness using a soluble metal salt precursor, such as the chloride, acetate, nitrate salt, following by reduction under hydrogen gas.

A preferred embodiment of the fifth process is a liquid phase reaction in which the DFF is dissolved in a suitable, inert solvent. The catalysts are placed in the solvent in a pressure vessel, and pressured to about 200-1000 psi, (1.4-6.9 MPa), more preferably about 500 psi (3.4 MPa) with an inert gas, preferably nitrogen. The reaction temperature is about 150° C.-250° C., more preferably about 200° C. The reaction product containing furan and furfural can be recycled through the process one or more times, to eventually form a reaction product consisting essentially of furan.

The above process can also be combined with the process to prepare DFF described above, to create a single integrated process wherein DFF is prepared using the metal bromide catalysts described above, then decarbonylated to furan or furfural.

Materials and Methods

HMF was obtained from Lancaster Synthesis, Windham, N.H. Unless otherwise stated, all materials were used as received without further purification. All percentages are by mole percent unless otherwise specified.

Examples 1-6

Reaction of HMF to DFF at Ambient Air
PRESSURE

In a cylindrical glass fitted with a stirrer and baffles, 0.165 g of cobalt(II) acetate tetrahydrate, 0.169 g of manganese(II) acetate tetrahydrate, 0.142 g of sodium bromide, 0.220 g biphenyl (GC internal standard), and 10.02 g of 5-hydroxymethyl(furfural) were admixed with 100 g of acetic. The solution was purged with nitrogen gas and the temperature raised to 75° C. using an external oil bath. The nitrogen was replaced with air at a flow rate of 100 ml/min at ambient atmospheric pressure. The vent oxygen was constantly monitored and occasionally liquid and vent gas samples for GC analysis were taken at the times shown in Table 2. After 30 hrs the reaction was terminated. The results from the liquid samples taken from the reactor during reaction of Example 1 are given in Table 1. The DFF yield increased with time to a maximum yield of 51% and then decreases thereafter. The mini-reactor data is summarized in Table 3. The rate of reaction, as given by the rate of disappearance of HMF, was dependent upon the concentration of the catalyst, see especially Examples 3, 4. The maximum yields and chemical species selectivities were also dependent on the concentration of the catalyst, see Examples 1, 3-6. The dependence of the selectivity on the concentration of catalyst is given in detail for Examples 3, 4, and 6 in Table 2. The formation of carbon dioxide and carbon monoxide are undesirable because they are caused by the decomposition of HMF and its products, as well as from the solvent, acetic acid. As can be seen in Table 2, increasing the catalyst concentration greatly decreases the formation of these carbon oxides. Example 4 combines the best yield, shortest reaction time, and one of the lowest rates of carbon oxide formation.

2,5-Diformylfuran was isolated from the reaction mass as follows. The liquid from the reaction mixture was allowed to evaporate. The residue after evaporation of the reaction mixture was (a) sublimed under vacuum, followed by recrystallization of the sublimate from toluene or cyclohexane; or (b) mixed with silica gel and extracted with hexanes or cyclohexane in a Soxhlet extractor; or (c) extracted with hot toluene, with subsequent filtration of the hot toluene solution through silica, evaporation of the filtrate, and recrystallization of the product from toluene or cyclohexane.

One specific example of isolation of DFF is as follows. The dark reaction mixture that was obtained from Example 5, was evaporated to dryness on a vacuum line. The resulting waxy green-tan material was transferred to a sublimation apparatus and sublimed under vacuum (10-50 millitorr) at 90° C. (oil bath) to produce 5.2 g (51 mol % based on initial HMF used) of DFF. The resulting DFF (95% pure; $^1$H NMR and GC-MS analysis) contained 3-5% of 5-acetoxymethylfurfural. DFF that was pure to the limits of spectroscopic detection was obtained by recrystallization of the sublimate from cyclohexane or toluene/hexanes. $^1$H NMR (CDCl$_3$, 25° C.), ppm: 7.4 (s; 2H; furane CH), 9.8 (s; 2H; CHO). $^{13}$C NMR (CD$_2$Cl$_2$, 25° C.), ppm: 120.4 (s; CH), 154.8 (s; q C), 179.7 (s, CHO). m/z=124. Alternatively, crude DFF can be purified by filtration of its concentrated dichloromethane solution through a short silica plug, followed by precipitation from the filtrate with hexanes.

TABLE 1

Formation of Diformylfuran in Example 1

| Time, min | Conversion, % | Selectivity, % | Yield, molar, % |
|---|---|---|---|
| 66 | 31.9 | 44.5 | 14.2 |
| 96 | 40.3 | 52.6 | 21.2 |
| 111 | 46.6 | 54.9 | 25.6 |
| 130 | 54.7 | 51.2 | 28.0 |
| 144 | 54.5 | 59.4 | 32.4 |
| 171 | 62.5 | 55.4 | 34.6 |
| 190 | 66.9 | 55.5 | 37.1 |
| 204 | 71.0 | 52.7 | 37.4 |
| 310 | 82.9 | 56.6 | 46.9 |
| 384 | 88.3 | 56.1 | 49.5 |
| 450 | 92.1 | 55.5 | 51.1 |
| 516 | 95.2 | 53.3 | 50.7 |
| 1368 | 100 | 35.1 | 35.1 |
| 1410 | 100 | 35.7 | 35.7 |
| 1728 | 100 | 19.8 | 19.8 |
| 1800 | 100 | 19.5 | 19.5 |

TABLE 2

Summary of Mini-reactor Oxygenations of Hydroxymethyl(furfural)

| | Ex. 1 | Ex. 2 | Ex. 3 | Ex. 4 | Ex. 5 | Ex. 6 |
|---|---|---|---|---|---|---|
| Temp, ° C. | 75 | 50 then 95 [5] | 75 | 75 | 50 then 75 [6] | 75 |
| HMF, g | 10.015 | 9.143 | 10.139 | 10.051 | 10.04 | 10.158 |
| HOAc, g | 100 | 100 | 100 | 100 | 100 | 100.1 |
| Co, M | 0.066 | 0.026 | 0.066 | 0.135 | 0.268 | 0.273 |
| Mn, M | 0.069 | 0.025 | 0.069 | 0.139 | 0.274 | 0.278 |
| Br, M | 0.137 | 0.050 | 0.137 | 0.279 | 0.557 | 0.580 |
| Zr, M | 0.005 | 0.000 | 0.005 | 0.005 | 0.005 | 0.005 |
| HMF rate, s$^{-1}$ [1] | 9.68E$^{-05}$ | 9.28E$^{-05}$ | 8.13E$^{-05}$ | 1.64E$^{-04}$ | — | 1.37E$^{-04}$ |
| HMF half-life | 119 | 124 | 142 | 70 | — | 84 |
| R2 | 0.998 | 0.878 | 0.972 | 0.999 | — | 0.994 |
| DFF Y, max [2] | 51 | 41 | 50 | 57 | 51 | 52 |
| Time, max | 450 | 414 | 642 | 310 | 550 | 430 |
| C, max | 92 | 98 | 95 | 91 | 95 | 97 |
| S, max | 55 | 42 | 53 | 63 | 54 | 54 |
| time, min [3] | 1800 | 564 | 640 | 366 | 550 | 430 |
| C, % | 100 | 99 | 95 | 95 | 95 | 97 |
| S, % | 19 | 41 | 53 | 58 | 54 | 54 |
| Y, % | 19 | 40 | 50 | 55 | 51 | 52 |
| HMF acet, % | 0.4 | 8.4 | 7.5 | 6.1 | 4.5 | 5.7 |
| CO$_X$, ml | 878 | — | 1022 | 257 | 219 | 318 |
| HMF to CO$_X$ [4] | 7.4 | — | 8.5 | 2.1 | 1.8 | 2.6 |

Footnotes
[1] Determined by rate of disappearance of hydroxymethyl(furfural).
[2] Abbreviations used: C = % conversion, S = % selectivity, Y = % molar yield, as determined by GC. Max is the highest observed during experiment.
[3] Time when experiment was terminated
[4] Loss of HMF due to carbon monoxide and carbon dioxide formation. Assumes no CO$_X$ formation from the solvent.
[5] Reaction performed at 50° C. for 105 min, then 95° C. for 459 min. Additional Co/Mn/Br catalyst was add at 115 and 210 min
[6] Reaction performed at 50° C. for 180 min, then 75° C. for 370 min

Examples 7-15

Reaction of HMF to DFF

Table 3 further illustrates that placing HMF with acetic acid and catalyst metals and then subjecting them to 1000 psi air pressure (7 MPa), can produce high yields of DFF. Molar yields up to 63% were obtained. The yield varied with temperature and type of catalyst used.

TABLE 3

Initial Conditions for the Oxidation of HMF in Shaker Tubes

| Ex. | Catalyst | HMF, g | Co, ppm | Mn, ppm | HBr, ppm | Zr, ppm | Temp, ° C. | Time, hr | HMF, conv., % | HMF, select. % | DFF yld, % |
|---|---|---|---|---|---|---|---|---|---|---|---|
| 7 | Co/Mn/Br/Zr | 0.2504 | 203 | 189 | 551 | 20 | 50 | 2 | 60.4 | 66.6 | 40.2 |
| 8 | Co/Mn/Br/Zr | 0.2481 | 406 | 378 | 1102 | 20 | 50 | 2 | 69.2 | 65.3 | 45.2 |

TABLE 3-continued

Initial Conditions for the Oxidation of HMF in Shaker Tubes

| Ex. | Catalyst | HMF, g | Co, ppm | Mn, ppm | HBr, ppm | Zr, ppm | Temp, °C. | Time, hr | HMF, conv., % | HMF, select. % | DFF yld, % |
|---|---|---|---|---|---|---|---|---|---|---|---|
| 9 | Co/Mn/Br | 0.2519 | 203 | 189 | 551 | 0 | 50 | 2 | 60.6 | 38.4 | 23.3 |
| 10 | Co/Mn/Br | 0.252 | 406 | 378 | 1102 | 0 | 50 | 2 | 61.7 | 54.6 | 33.7 |
| 11 | Co | 0.2516 | 7000 | 0 | 0 | 0 | 50 | 2 | 48.3 | 22.8 | 11.0 |
| 12 | Co/Mn/Br/Zr | 0.25 | 203 | 189 | 551 | 20 | 75 | 2 | 82.5 | 73.2 | 60.4 |
| 13 | Co/Mn/Br/Zr | 0.2517 | 406 | 378 | 1102 | 20 | 75 | 2 | 99.7 | 61.6 | 61.4 |
| 14 | Co/Mn/Br | 0.2529 | 203 | 189 | 551 | 0 | 75 | 2 | 71 | 54.3 | 38.6 |
| 15 | Co/Mn/Br | 0.2514 | 406 | 378 | 1102 | 0 | 75 | 2 | 92.2 | 68.3 | 63.0 |

Examples 16-40

The Reaction of HMF to CFF and FDA

Placing HMF in reactors with acetic acid and catalyst metals and having them react with air at 1000 psi (7 MPa) gave good yields of FDA. A particular advantage of this method is that the majority of FDA precipitates from solution upon cooling to room temperature. The yields to CFF and FDA, reported on Table 4, are those which were obtained from the solids only. Table 4 illustrates that different catalysts such as those using cobalt, or a mixture such as Co/Mn/Br and Co/Mn/Zr/Br all produced good yields of FDA. It also illustrates that increasing catalyst concentrations at a given temperature and time, nearly always increased the FDA yield.

Examples 35 through 37 are to be compared to Examples 38 through 40. In the latter series the temperature was staged—initially it was held at 75° C. for 2 hrs and then raised to 150° C. for two hrs. This staging of the temperature gave higher yields.

Examples 41-59

Oxidation of Benzyl Alcohol 0.247 g of cobalt(II) acetate tetrahydrate, 0.242 g of manganese(II) acetate tetrahydrate, 0.337 g of hydrogen bromide, 0.198 g biphenyl (GC internal standard), and 9.72 g of benzyl alcohol were placed in 95 g of acetic acid and 5% water in a cylindrical glass flask fitted with a stirrer and baffles. The solution was purged with nitrogen gas and the temperature raised to 95° C. using an external oil bath. The nitrogen was replaced with air at a flow rate of 100 ml/min at ambient atmospheric pressure. Samples were withdrawn from the reactor and analyzed giving the results in Table 5. A yield of 55 mol percent benzaldehyde is observed. (Values of benzaldehyde, benzyl acetate, benzoic acid in mol % based on benzyl alcohol charged).

TABLE 4

Reaction of HMF to CFF and FDA All reactions at 1000 psi air (7 MPa)

| Ex. | Catalyst | HMF, g | Co, ppm | Mn, ppm | HBr, Ppm | Zr, ppm | Temp, C. | Time, hr | CFF, yld | FDA, yld |
|---|---|---|---|---|---|---|---|---|---|---|
| 16 | Co/Mn/Br/Zr | 0.2517 | 203 | 189 | 551 | 20 | 100 | 2 | 3.1 | 18.7 |
| 17 | Co/Mn/Br/Zr | 0.2533 | 406 | 378 | 1102 | 20 | 100 | 2 | 6.8 | 42.3 |
| 18 | Co/Mn/Br | 0.2522 | 203 | 189 | 551 | 0 | 100 | 2 | 4.1 | 29.7 |
| 19 | Co/Mn/Br | 0.2505 | 406 | 378 | 1102 | 0 | 100 | 2 | 3.3 | 44.8 |
| 20 | Co | 0.2589 | 7000 | 0 | 0 | 0 | 100 | 2 | 5.1 | 31.0 |
| 21 | Co/Mn/Br/Zr | 0.2483 | 203 | 189 | 551 | 20 | 125 | 2 | 2.1 | 36.5 |
| 22 | Co/Mn/Br/Zr | 0.249 | 406 | 378 | 1102 | 20 | 125 | 2 | 2.3 | 45.6 |
| 23 | Co/Mn/Br | 0.2503 | 203 | 189 | 551 | 0 | 125 | 2 | 1.8 | 35.2 |
| 24 | Co/Mn/Br | 0.2526 | 406 | 378 | 1102 | 0 | 125 | 2 | 2.2 | 44.7 |
| 25 | Co | 0.2616 | 7000 | 0 | 0 | 0 | 125 | 2 | 4.3 | 16.8 |
| 26 | Co/Mn/Br/Zr | 0.7535 | 406 | 378 | 1102 | 20 | 105 | 12 | 3.1 | 26.4 |
| 27 | Co/Mn/Br/Zr | 0.7568 | 812 | 756 | 2204 | 20 | 105 | 12 | 4.2 | 50.6 |
| 28 | Co/Mn/Br/Zr | 0.7498 | 1218 | 1134 | 3306 | 20 | 105 | 12 | 2.5 | 58.8 |
| 29 | Co/Mn/Br/Zr | 0.5057 | 406 | 378 | 1102 | 20 | 105 | 12 | 2.4 | 24.1 |
| 30 | Co/Mn/Br/Zr | 0.501 | 812 | 756 | 2204 | 20 | 105 | 12 | 5.1 | 44.0 |
| 31 | Co/Mn/Br/Zr | 0.4994 | 1218 | 1134 | 3306 | 20 | 105 | 12 | 5.6 | 47.4 |
| 32 | Co/Mn/Br/Zr | 0.499 | 406 | 378 | 1102 | 20 | 105 | 8 | 3.3 | 32.9 |
| 33 | Co/Mn/Br/Zr | 0.5046 | 812 | 756 | 2204 | 20 | 105 | 8 | 4.8 | 41.0 |
| 34 | Co/Mn/Br/Zr | 0.5 | 1218 | 1134 | 3306 | 20 | 105 | 8 | 7.3 | 50.6 |
| 35 | Co/Mn/Br/Zr | 0.2498 | 406 | 378 | 1102 | 20 | 105 | 2 | 3.7 | 36.9 |
| 36 | Co/Mn/Br/Zr | 0.254 | 812 | 756 | 2204 | 20 | 105 | 2 | 4.8 | 40.9 |
| 37 | Co/Mn/Br/Zr | 0.4988 | 406 | 378 | 1102 | 20 | 105 | 2 | 1.7 | 14.0 |
| 38 | Co/Mn/Br/Zr | 0.2517 | 406 | 378 | 1102 | 20 | 75, 150 | 2, 2 | 5.2 | 51.4 |
| 39 | Co/Mn/Br/Zr | 0.5077 | 812 | 756 | 2204 | 20 | 75, 150 | 2, 2 | 6.2 | 52.9 |
| 40 | Co/Mn/Br/Zr | 0.5105 | 406 | 378 | 1102 | 20 | 75, 150 | 2, 2 | 6.5 | 54.6 |

TABLE 5

Oxidation of Benzyl Alcohol

| Ex. | Time, hr. | Conv., % | Benzaldehyde, mol % | Benzyl acetate, mol % | Benzoic acid, mol % |
|---|---|---|---|---|---|
| 41 | 0 | 10.4 | 0.36 | 10.9 | 0 |
| 42 | 0.1 | 15 | 1.8 | 11.3 | 0 |
| 43 | 0.2 | 21 | 5.5 | 12.9 | 0 |
| 44 | 0.33 | 28 | 10.4 | 15.1 | 0 |
| 45 | 0.5 | 35 | 15 | 16.8 | 0 |
| 46 | 0.6 | 41 | 19.2 | 18.2 | 0 |
| 47 | 0.67 | 44 | 21.1 | 18.9 | 0.27 |
| 48 | 0.75 | 48 | 24.3 | 19.6 | 0.35 |
| 49 | 0.87 | 52 | 27.3 | 20.4 | 0.45 |
| 50 | 1 | 57 | 31.5 | 21.5 | 0.61 |
| 51 | 1.17 | 62 | 34.1 | 22 | 0.8 |
| 52 | 1.3 | 67 | 37.8 | 22.8 | 1.02 |
| 53 | 1.4 | 69 | 39.7 | 23.1 | 1.21 |
| 54 | 1.53 | 73 | 42 | 23.5 | 1.55 |
| 55 | 1.75 | 78 | 45.4 | 24.1 | 1.75 |
| 56 | 1.92 | 81 | 47.6 | 24.3 | 2.45 |
| 57 | 2.1 | 83 | 49.3 | 24.5 | 2.69 |
| 58 | 2.33 | 88 | 52.4 | 24.6 | 3.43 |
| 59 | 2.83 | 93 | 54.6 | 24.2 | 6.23 |

Example 60

Polymerization of DFF of
5-(hydroxymethyl)-furan-2-carboxylic acid
('Tishchenko Polymerization')

The reaction was conducted under rigorously dry conditions. The products were isolated in air. To a mixture of DFF (0.265 g) and dry toluene (6 mL) was added aluminum isopropoxide (Aldrich; 45 mg), and the reaction mixture was vigorously stirred at 95° C. (oil bath) for 3 hours. The greenish-brown precipitate was filtered off, washed with toluene, and dried under vacuum to give 0.190 g of a tan powder that appeared to be amorphous (fraction A). The combined mother liquor and the washings were evaporated and dried under vacuum to yield 0.105 g of fraction B as a viscous yellowish oil. $^1$H NMR spectra of both fractions A and B (CDCl$_3$, 25° C.) revealed a number of singlets at 5.2-5.4 ppm (—CH$_2$—O(O)C—), indicative of polyester formation. A sample of the solid product (0.7460 mg) was studied by TGA in the temperature range of 40-600° C. The onset of decomposition was observed around 100-120° C. The total weight loss measured was about 10% at 147° C., and about 34% at 294° C.

Example 61

The reaction was carried out under nitrogen. The Shvo catalyst ([(Ph$_4$C$_5$OHOC$_5$Ph$_4$)Ru$_2$(CO)$_4$($^-$H)]; as described in Menashe, N.; Shvo, Y. Organometallics 1991, 10, 3885; 5 mg) was added to a mixture of DFF (200 mg), toluene (5 mL), and formic acid (cocatalyst; 5 L). The clear solution was stirred at 100° C. (oil bath) for 3 hours. $^1$H NMR analysis of the reaction mixture indicated 50% conversion to polymeric material. More Shvo catalyst (3 mg) was added and the mixture was stirred at 100° C. (oil bath) for 2 days, 90% conversion was reached ($^1$H NMR).

Examples 62-69

The catalysts were prepared by taking a carbon support (Englehard Corp., 12 Thompson Rd., E. Windsor, Conn.) and impregnating by incipient wetness a metal salt. The precursors used were NiCl$_2$.6H$_2$O (Alfa), Re$_2$O$_7$ (Alfa), PdCl$_2$ (Alfa), RuCl$_3$.xH$_2$O (Aldrich), H$_2$PtCl$_6$ (Johnson Matthey), CrCl$_3$.6H$_2$O (Baker), and 5% Rh using RhCl$_3$.xH$_2$O (Alfa). The samples were dried and reduced at 400° C. in H$_2$ for 2 hours. The decarbonylation reactions were performed by dissolving 50 mg of DFF in 1 ml of dioxane, and which was then placed with 50 mg of catalyst in a 5 ml pressure vessel. The vessel was charged to 500 psi with N$_2$ and heated to 200° C. for 2 hours. The sample was then cooled, vented and the product analyzed by GC-MS. Results are shown in Table 6 below.

TABLE 6

Decarbonylation of DFF

| | | | Selectivity (%) | | | |
|---|---|---|---|---|---|---|
| Ex. | Catalyst | Conv. (%) | Furan | THF | Furfural | Others |
| 62 | 5% Re/carbon | 15.6 | 2.8 | 0.0 | 2.1 | 95.1 |
| 63 | 5% Pt/carbon | 46.1 | 2.2 | 0.0 | 42.7 | 55.0 |
| 64 | 5% Cr/carbon | 27.3 | 1.3 | 0.0 | 0.0 | 98.7 |
| 65 | 5% Rh/carbon | 33.8 | 1.7 | 0.0 | 29.7 | 68.6 |
| 66 | 5% Ni/carbon | 10.3 | 5.1 | 0.0 | 1.7 | 93.2 |
| 67 | 5% Pd/carbon | 98.6 | 49.8 | 1.0 | 48.1 | 1.1 |
| 68 | 5% Ru/carbon | 25.0 | 3.5 | 0.0 | 62.9 | 33.6 |

What is claimed is:

1. A process for the preparation of a diacid of the formula HOOC—R'—COOH from an alcohol/aldehyde of the formula HOH$_2$C—R'—(C=O)H, wherein R' is an optionally substituted furan ring, comprising the steps:
    (a) contacting the alcohol/aldehyde with an oxidant in the presence of a metal bromide catalyst forming a dialdehyde having the formula H(C=O)—R'—(C=O)H, and optionally isolating the dialdehyde;
    (b) contacting the dialdehyde with an oxidant in the presence of a metal bromide catalyst forming an acid/aldehyde having the formula HOOC—R'—(C=O)H, and optionally isolating the acid/aldehyde; and
    (c) contacting the acid/dialdehyde with an oxidant in the presence of a metal bromide catalyst forming the diacid, and optionally isolating the diacid.

2. The process of claim 1 wherein the product of the reaction is isolated following steps a, b or c.

3. The process of claim 1 wherein the process is run in a solvent or solvent mixture comprising at least one aliphatic C$_2$-C$_6$ monocarboxylic acid solvent compound.

4. The process of claim 3 wherein the process is run in acetic acid.

5. The process of claim 3 wherein the metal bromide catalyst comprises a source of bromine and at least one metal selected from the group consisting of Co and Mn.

6. The process of claim 5 wherein the metal bromide catalyst further comprises Zr.

7. The process of claim 6 wherein the catalyst comprises Co and Mn.

8. The process of claim 4 wherein the process further comprises converting the alcohol/aldehyde of the formula HOH$_2$C—R'—(C=O)H to an acetate ester of the formula CH$_3$(C=O)OCH$_2$—R'—(C=O)H.

9. The process of claim 8 wherein the diacid is furan-2,5-dicarboxylic acid and the alcohol/aldehyde is 5-(hydroxymethyl)furfural.

* * * * *